United States Patent [19]

Fauran et al.

[11] 4,029,789
[45] June 14, 1977

[54] 1-[2'-(α-FUROYL OR α-THIENOYL)ETH-1'-YL]-2-(4''-CINNAMYL PIPERAZIN-1''-YL METHYL)BENZIMIDAZOLES AND METHOD OF USING SAME

[75] Inventors: Claude P. Fauran; Nicole Dorme; Guy M. Raynaud, all of Paris; Jeannine Eberle, Chatou, all of France

[73] Assignee: Delalande S.A., Courbevoie, France

[22] Filed: Nov. 20, 1975

[21] Appl. No.: 633,960

[30] Foreign Application Priority Data
Nov. 21, 1974 France .................. 74.38292

[52] U.S. Cl. .................. 424/250; 260/240 K; 260/309.2
[51] Int. Cl.² .................. A61K 31/34; A61K 31/38
[58] Field of Search .................. 260/240 K; 424/250

[56] References Cited
UNITED STATES PATENTS

| 3,362,956 | 1/1968 | Archer | 260/268 |
| 3,472,854 | 10/1969 | Archer | 260/268 |
| 3,862,177 | 1/1975 | Fauran et al. | 260/240 K |

Primary Examiner—John D. Randolph
Attorney, Agent, or Firm—Woodhams, Blanchard and Flynn

[57] ABSTRACT

Compounds of the formula

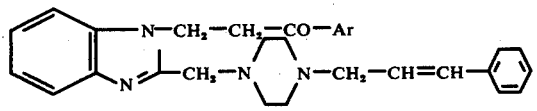

in which Ar is α-furyl or α-thienyl and pharmacologically acceptable salts thereof are provided as novel therapeutic agents which have inter alia utility in treating asthma, respiratory deficiency, visceral spasms, gastroduodenal ulcers or hyperchlorhydria.

7 Claims, No Drawings

1-[2'-(α-FUROYL OR α-THIENOYL)ETH-1'-YL]-2-(4'''-CINNAMYL PIPERAZIN-1''-YL METHYL)BENZIMIDAZOLES AND METHOD OF USING SAME

The present application concerns novel compounds having the general formula (I):

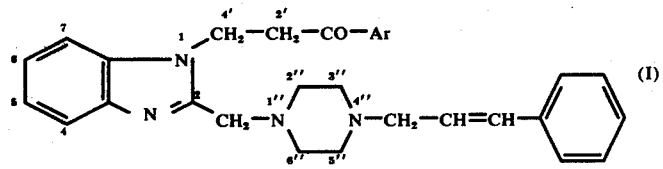

in which Ar represents an α-furyl or α-thienyl radical.

The process of preparation of the compounds in accordance with the present invention consists in alkylating a monosubstituted piperazine having the formula (II):

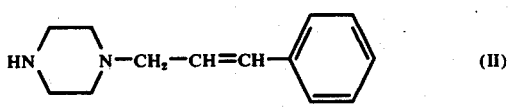

by means of a benzimidazole having the formula (III):

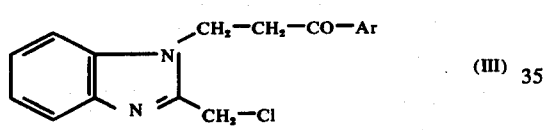

where Ar has the same significance as in the general formula (I).

The compounds of formula (III) are novel and are obtained by halogenation of a compound of formula (IV):

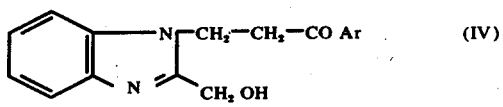

by means of thionyl chloride of formula (V):

Finally, the compounds of formula (IV) are also novel resulting from the alkylation of benzimidazol-2 yl methanol having the formula (VI):

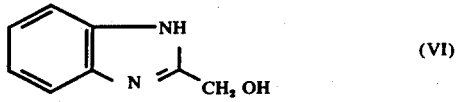

by a Mannich base of formula (VII):

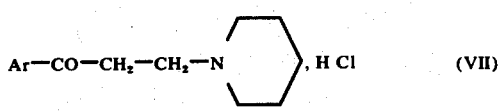

where Ar has the same significance as in the formula (I).

Given below are the preparations of the compounds according to the invention, obtained in the form of their dimaleate.

Preparation of the dimaleate of 1-[2'-(α-furoyl) eth-1' yl] -2-(4''-cinnamyl piperazin-1'' yl methyl)benzimidazole. code number 73 0457

. 1st step: 1-[2'-(α-furoyl) eth-1'yl] benzimidazol-2 yl methanol

Code number: 73 0460

To a solution of 0.7 mole of α-furyl piperidinoethyl ketone hydrochloride in 750 ml of ethanol and 500 ml of water, is added 0.64 mole of benzimidazol-2 yl methanol. After a reflux for 4 hours, the reaction medium is frozen, then filtered.

The compound obtained is purified by recrystallisation in absolute alcohol.
- melting point : 155° C
- Yield : 56%

. 2nd step: 1-[2'-(α-furoyl) eth-1'yl]-2-chloromethyl benzimidazole

Code number : 73 0461

To a suspension of 0.18 mole of compound code number 73 0460 obtained in the first step, in 140 ml of anhydrous chloroform, is added within 1 hour and at 0° C, 0.36 mole of thionyl chloride in solution in 100 ml of anhydrous chloroform. After contacting for 1 hour 30 minutes with return to the ambient temperature, the chloroform is evaporated. The evaporation residue is taken up with methanol and neutralised with sodium bicarbonate. Then the methanol is evaporated, the evaporation residue is taken up with a water-chloroform mixture, followed by decantation and evaporation.

The raw product obtained is purified by recrystallisation in isopropyl alcohol.
- Melting point : 128° C;
- Yield : 73%.

. 3rd step: dimaleate of 1-[2'-(α-furoyl) eth-1' yl]-2-(4''-cinnamyl piperazin-1'' yl methyl) benzimidazole Code number : 73 0457

To a mixture of 0.1 mole of compound code number 73 0461 obtained in the second step, in 150 ml of ethyl acetate, is added 0.15 mole of sodium carbonate, then 0.12 mole of 1-cinnamyl piperazine. After a reflux for 1 hour, the reaction medium is taken up with hot water. It is left to decant, the ethyl acetate phase is dried and the ethyl acetate evaporated.

The product obtained is salified by means of 0.2 mole of maleic acid.
- Melting point : 180° C;
- Yield : 72%; O
- Empirical formula : $C_{36}H_{38}N_4O_{10}$;

- Elementary analysis.

|            |     | C     | H    | N    |
|------------|-----|-------|------|------|
| Calculated | (%) | 62.96 | 5.58 | 8.16 |
| Found      | (%) | 63.16 | 5.59 | 7.95 |

Preparation of dimaleate of 1-[2'-(α-thienoyl) eth-1'yl]-2-(4''-cinnamyl piperazin-1'' yl methyl) benzimidazole Code number : 73 0466

. 1st step : 1-[2'-(α-thienoyl) eth-1'yl]benzimidazol-2 yl methanol.

Code number 73 0468

To a solution of 0.7 mole of α-thienyl piperidinoethyl ketone hydrochloride in 750 ml of ethanol and 500 ml of water, was added 0.64 mole of benzimidazol-2 yl methanol. After a reflux for 4 hours, the reaction medium was frozen, then filtered.

The compound obtained was purified by recrystallisation in ethanol.
- Melting point : 150° C,
- Yield : 55%.

2nd step : 1-[2'-(α-thienoyl) eth-1'yl]-2-chloromethyl-2 benzimidazole

Code number : 73 0469.

To a suspension of 0.2 mole of compound code number 73 0468 obtained in the previous step, in 160 ml of anhydrous chloroform, is added at 0° C and within 1 hour, 0.4 mole of thionyl chloride in solution in 120 ml of anhydrous chloroform. After contacting for 2 hours with return to the ambient temperature, the chloroform is evaporated. The evaporation residue is taken up with methanol and neutralised with sodium bicarbonate. Then the methanol is evaporated, the evacuation residue is taken up with water and chloroform, followed by decantation and evaporation.

The raw product is purified by recrystallisation in isopropyl alcohol.
- Melting point : 143° C,
- Yield : 60%.

3rd step: dimaleate of 1-[2'(α-thienoyl) eth-1'yl]-2-(4''-cinnamyl piperazin-1''yl methyl)benzimidazole.

Code number : 73 0466

To a solution of 0.11 mole of compound code number 73 0469 obtained in the preceding step, in 150 ml of ethyl acetate, was added 0.15 mole of sodium carbonate, then 0.13 mole of 1-cinnamyl piperazine in solution in 80 ml of ethyl acetate. After a reflux for 1 hour, the reaction medium was taken up with hot water. It was left to decant, the ethyl acetate phase was dried and the ethyl acetate evaporated.

The raw product was salified in acetone by means of 0.2 mole of maleic acid.
- Melting point : 175° C;
- Yield : 72%;
- Empirical formula : $C_{36}H_{38}N_4O_9S$;
- Elementary analysis.

|            |     | C     | H    | N    |
|------------|-----|-------|------|------|
| Calculated | (%) | 61.52 | 5.45 | 7.97 |
| Found      | (%) | 61.48 | 5.58 | 7.67 |

The compounds of formula (I) were tested on laboratory animals and showed anti-bronchoconstriction, respiratory analeptic, spasmolytic, anti-ulcerous and gastric antisecretory properties.

1. Anti-bronchoconstriction properties

Injected intravenously or intraduodenally, the compounds of formula (I) are capable of opposing bronchoconstriction caused in a guinea-pig anaesthetized with ethylurethane at 20% (1.5 g/kg intraperitoneally) by intravenous injection of histamine (10 μ/kg/i.v.), of acetylcholine (40 μg/kg/i.v.), of bradykinine (5 μg/kg/i.v.) or of serotinine (20 μg/kg/i.v.).

These properties are also observed by administering the compounds of formula (I) orally, to a vigil guinea-pig subjected to a histamine aerosol (exposition for 10 minutes to an aerosol obtained from an aqueous solution containing 0.4% histamine and 10% glycerine), the criterium of activity being the total protection from the fall caused by the bronchospasm.

The results obtained by the administration of the compounds of formula (I) are listed in Table I following:

TABLE I

| Code number of compound tested | Broncho-constricting agent | Dose administered or DE 50 | Percentage of inhibition of the broncho-constriction (%) | Duration |
|---|---|---|---|---|
| 73 0457 | Histamine aerosol | 100 mg/kg/p.o. | 100 | >6 hours |
|  | Histamine | DE 50 : 0.5 mg/kg/iv | −15 to 50 mn |  |
|  |  | 12.5 mg/kg/id | 100 | 120 to 180 mn |
|  | Acetyl-choline | DE 50<4 mg/kg/iv | — | — |
|  |  | 12.5 mg/kg/id | 70 | >90 minutes |
|  | Brady-kinine | 8 mg/kg/iv | 75 | — |
|  | Serotonine | DE 50<4 mg/kg/iv | — | — |
|  | Acetyl-choline | 100 mg/kg/id | 100 | 1 hour |
| 73 0466 | Histamine | 25 mg/kg/id | 50 | — |

2. Respiratory analeptic properties

The compounds of formula (I) administered intravenously to a vigil rabbit, are capable of opposing morphinic respiratory depression (subcutaneous injection of 50 mg/kg of morphine hydrochloride).

Table II above compares the results obtained with the compound of code number 73 0457 and a well-known respiratory analeptic, prethcamide sold under the trademark MICORENE.

TABLE II

| Compound tested | Dose administered (mg/kg/iv) | Percentage increase (%) Respiratory frequency | Percentage increase (%) Respiratory amplitude | Duration of effect (min) | Dose administered DL 50 (mouse) |
|---|---|---|---|---|---|
| 73 0457 | 10 | +130 | +80 | 25 | < 10/2000 |
| MICORENE | 10 | +47 | +70 | 7 | 10/1000 |

It is obvious from this comparison that the compound of the invention is a respiratory analeptic superior to prethcamide (MICORENE).

3. Spasmolytic properties

Compound code number 73 0457, introduced into the conserving medium, is capable of opposing the contractural action of histamine and bradykinine on the ileum of a guinea-pig, DI 50 being respectively 0.16 μg/ml and 3.1 μg/ml, prevents spasms in the uterus of a female rat induced by serotonine (DI 50 = 0.8 μg/ml) and opposes the contracting effect of acetylcholine on the duodenum of a rat (DI 50 = 0.8 μg/ml).

4. Anti-ulcerous properties a. Constraint ulcers: the compounds of formula (I), administered orally, reduce the area of ulcerations caused in a rat placed under constraint. Thus, compound No 73 0466 administered at a dose of 5 mg/kg/po, reduces by 78% the area of the ulcerations caused by being put under constraint for 7 hours.

b. Shay's ulcers: the compounds of formula (I) administered intraduodenally reduce the area of ulcerations induce in a rat by binding the pylorus. Thus, compound code No 73 0466 administered in a dose of 20 mg/kg/i.d. reduces by 80% Shay's ulcer.

5. Gastric antisecretory properties

The compounds of formula (I), administered intraduodenally to an anaesthetized rat provided with a Shay binding are capable of reducing the gastric secretion.

As an example, compound No 73 0466 administered as a dose of 2 mg/kg/i.d. reduces by 28% the volume of the gastric secretion.

Moreover, since the compounds of formula (I) are not very toxic, as that comes out from table III following, the divergence between the pharmacologically active and lethal doses is sufficient with these compounds to permit their use in therapeutics.

TABLE III

| Code No. of Compound tested | Dose administered (mouse) Orally (mg/kg) | Dose administered (mouse) Intravenously DE 50(mg/kg) | Percentage mortality (%) Orally | Percentage mortality (%) Intravenously |
|---|---|---|---|---|
| 73 0457 | 2 000 | 48 ± 2.5 | 0 | ≃ 50 |
| 73 0466 | 2 000 | — | 30 | — |

The compounds of formula (I) are indicated in the treatment of asthma, respiratory deficiency, visceral spasms, gastroduodenal ulcers and hyperchlorhydria.

They are administered orally in the form of tablets, pills or gelules containing 50 to 400 mg of active ingredient (1 to 5 per day), in the form of drops containing 0.5 to 5% of active ingredient (20 to 60 drops — 1 to 3 times a day), parenterally in the form of injectable ampoules containing 10 to 250 mg of active ingredient (1 to 3 per day).

Furthermore, the anti-bronchoconstriction and respiratory analeptic activity, on the one hand, and the gastric-antisecretory and anti-ulcerous activity on the other hand, were compared with the activities of a compound representative of the compounds described in the U.S. Pat. No. 3 862 177 belonging to the applicant, this compound having the following formula:

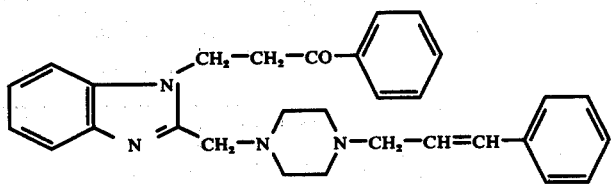

and having code number 7 110.

A. Anti-bronchoconstriction and respiratory analeptic property

.- The anti-bronchoconstriction properties were studied in an anaesthetized guinea-pig and in a vigil guinea-pig.

- In an anaesthetized guinea-pig

The antagonism exercised by the products studied to a bronchoconstriction due to an intravenous injection of acetylcholine, histamine or bradykinine was evaluated according to Konzett and Rossler's method.

The products studied were administered intraduodenally or intravenously.

- In a vigil guinea-pig

The activity of the orally administered products studied was evaluated by the percentage of animals totally protected against the fall caused by a bronchospasm, obtained by exposing the guinea-pigs to an acetylcholine or histamine aerosol.

.- Respiratory analeptic properties were studied in a vigil rabbit subjected to a morphinic respiratory depression. The products studied were administered intravenously.

The results obtained are given in the following tables IV and V.

.- The anti-ulcerous activity was evaluated by the percentage of protection (quantal response) against ulcers caused in a rat by binding the pylorus or by putting under constraint for 7 hours.

The products were administered intraduodenally (Shay's ulcer) or orally (constraint ulcer). The results

TABLE IV

| Pharmacological test | | | Compound of the invention | | Compound of patent No 3 862 177 |
|---|---|---|---|---|---|
| Acute toxicity-mouse. (p.o.) | | | 73 0457 | 73 0466 | 7 110 |
| | | | 0 % at 2 000 | 30 % at 2 000 | 30 % at 4 800 |
| Anti-bron-cho-con-stric-tion action | Anes-thetized (i.v.) guinea-pig | Acetylcholine | i.v. 0.0625—→63 % > 2 H 30 | | i.v. 2.4 = D.E. 50 |
| | | Histamine (i.v.) | i.d. 12.5—→70 % > 90 min | i.d. 25—→95 % > 30 min | i.d. 30—→0 |
| | | Bradykinine (i.v.) | i.v. 0.0625 = D.E. 50 | i.d. 25 = D.E. 50 | — |
| | Vigil guinea-pig | Acetylcholine (aerosol) | i.v. 8—→75 % | — | i.d. 30 = D.E. 50 |
| | | | p.o. 12.5—→50 % | p.o. 50—→100 % | |
| | | Histamine (aerosol) | p.o. 1.56—→50 % | p.o. 50—→67 % | — |

The doses are expressed in mg/kg (p.o. = orally, i.v. = intravenously, i.d. = intraduodenally)

TABLE V

| Compound tested | Dose administered (mg/kg/i.v.) | Percentage increase (%) | | Duration of effect (min.) |
|---|---|---|---|---|
| | | Respiratory frequency | Respiratory amplitude | |
| Compound of the invention 73 0457 | 10 | + 130 | + 80 | 25 |
| Compound of the patent No. 3 862 177 | 4 | 0 | 0 | 0 |

Compared to the compound of the patent No 3 862 obtained are given in Table VI.

TABLE VI

| Pharmacological activity | Compounds tested | Manner of admin. | 73 0457 | 73 0466 | 7110 |
|---|---|---|---|---|---|
| Gastric antisecretory action | Volume | id | 11.5 = D.E. 50 | 2 (− 28 %) | 2.5 = D.E. 50 |
| | Free acid concentration | id | 55 = D.E. 50 | 2 inactive | 4.5 (− 53 %) |
| | Free acid flow | id | 15 = D.E. 50 | 2 (− 30 %) | 1.5 (− 43 %) |
| Anti-ulcerous action | Shay's ulcer | id | 50 0 | 20 − 33 % | 28.5 = D.E. 50 |
| | Constraint ulcer for 7 hours. | po | 50 − 63 % | 5 − 38 % | 4.2 = D.E. 50 |

The doses are expressed in mg/kg
i.d. = intravenously
p.o. = orally 177 the two compounds of the invention, carriers of an α-furyl or α-thienyl radical, possess anti-bronchoconstriction properties more lasting and more effective at lower doses. Thus, in the case of a bronchoconstriction caused by acetylcholine in an anaesthetized guinea-pig, compound No. 73 0457 acts at a dose 38 times lower than that of compound No. 7110.

Moreover, compounds No. 73 0457 and 73 0466 are active in this same test, not only when administered intravenously but intraduodenally, whereas compound No. 7110 acts solely intravenously.

Compound No. 73 0457 is moreover differentiated from compound No. 7110 by its considerable respiratory analeptic activity.

B. Gastric antisecretory and antiulcerous activity

.- The gastric antisecretory activity was studied in a vigil rat fitted with a pyloric binding for 4 hours, according to Shay and al.

It was evaluated by diminutions in the volume, the concentration and the flow of free acid in the gastric juice. The compounds tested were administered intraduodenally.

In comparison with compound No. 7110, the compounds tested according to the invention show inferior antisecretory and anti-ulcerous properties.

Finally, compounds No. 73 0457 and 73 0466 are differentiated from the compounds of the U.S. patent No 3 862 177 by their considerable anti-bronchoconstriction and respiratory analeptic properties as well as their lower gastric antisecretory and anti-ulcerous activities.

The compounds of the invention are then indicated especially for the treatment of respiratory infections (asthma, . . . .) whereas the compounds of the parent application are indicated essentially for anti-ulcerous therapeutics.

What we claim is:

1. A compound having the formula

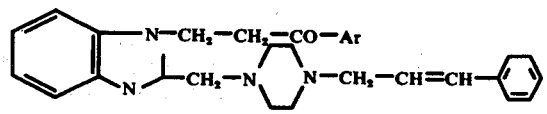

in which Ar is α-furyl or α-thienyl, and the pharmacologically acceptable acid addition salts thereof.

2. A compound as claimed in claim 1 in which Ar is α-furyl.

3. The dimaleate salt of the compound claimed in claim 2.

4. A compound as claimed in claim 1 in which Ar is α-thienyl.

5. The dimaleate salt of the compound claimed in claim 4.

6. A composition for treating a condition of asthma, respiratory deficiency, visceral spasms, gastroduodenal ulcers or hyperchlorhydria, comprising an effective amount of a compound as claimed in claim 1 for treating the condition, together with a pharmaceutically acceptable carrier.

7. A method for treating asthma which comprises administering to a host suffering from asthma a therapeutically effective amount of a compound as claimed in claim 1, with a pharmaceutically acceptable base.

* * * * *

UNITED STATES PATENT AND TRADEMARK OFFICE
CERTIFICATE OF CORRECTION

PATENT NO. : 4 029 789
DATED : June 14, 1977
INVENTOR(S) : Claude P. Fauran, Nicole Dorme, Guy M. Raynaud and Jeannine Eberle It is certified that error appears in the above-identified patent and that said Letters Patent are hereby corrected as shown below:

Please change the formula of Claim 1 to read as follows:

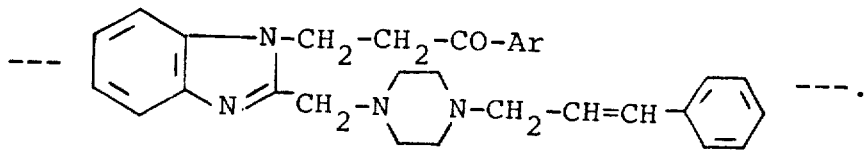

Signed and Sealed this

Twentieth Day of September 1977

[SEAL]

Attest:

RUTH C. MASON
Attesting Officer

LUTRELLE F. PARKER
Acting Commissioner of Patents and Trademarks